US012387319B2

(12) United States Patent
Zhang et al.

(10) Patent No.: US 12,387,319 B2
(45) Date of Patent: Aug. 12, 2025

(54) SYSTEMS AND METHODS FOR ACNE COUNTING, LOCALIZATION AND VISUALIZATION

(71) Applicant: L'Oreal, Paris (FR)

(72) Inventors: Yuze Zhang, Scarborough (CA); Ruowei Jiang, Toronto (CA); Parham Aarabi, Richmond Hill (CA)

(73) Assignee: L'Oreal, Paris (FR)

( * ) Notice: Subject to any disclaimer, the term of this patent is extended or adjusted under 35 U.S.C. 154(b) by 729 days.

(21) Appl. No.: 17/491,623

(22) Filed: Oct. 1, 2021

(65) Prior Publication Data

US 2022/0108445 A1 Apr. 7, 2022

Related U.S. Application Data

(60) Provisional application No. 63/086,694, filed on Oct. 2, 2020.

(30) Foreign Application Priority Data

Dec. 10, 2020 (FR) ...................................... 2013002

(51) Int. Cl.
*G06T 7/00* (2017.01)
*A61B 5/00* (2006.01)

(52) U.S. Cl.
CPC ............ *G06T 7/0012* (2013.01); *A61B 5/441* (2013.01); *G06T 2207/20081* (2013.01);
(Continued)

(58) Field of Classification Search
CPC ......... G06T 7/0012; G06T 2207/20081; G06T 2207/20084; G06T 2207/30088; G06T 2207/30201; A61B 5/441
See application file for complete search history.

(56) References Cited

U.S. PATENT DOCUMENTS

| | | | | |
|---|---|---|---|---|
| 2020/0160980 A1* | 5/2020 | Lyman | .................... | G06N 3/045 |
| 2020/0380674 A1* | 12/2020 | Ding | .................... | G06T 7/0012 |
| 2021/0357644 A1* | 11/2021 | Jain | ...................... | G06V 10/764 |

FOREIGN PATENT DOCUMENTS

| CN | 112037162 A | 12/2020 |
|---|---|---|
| JP | 2004-38918 A | 2/2004 |

(Continued)

OTHER PUBLICATIONS

Maroni et al., "Automated Detection, Extraction and Counting of Acne Lesions for Automatic Evaluation and Tracking of Acne Severity" (published in 2017 IEEE Symposium Series on Computational Intelligence (SSCI), Nov./Dec. 2017).*

(Continued)

*Primary Examiner* — Casey L Kretzer
(74) *Attorney, Agent, or Firm* — Oblon, McClelland, Maier & Neustadt, L.L.P.

(57) ABSTRACT

Systems, methods and techniques provide for acne localization, counting and visualization. An image is processed using a trained model to identify objects. The model may be a deep learning (e.g. convolutional neural) network configured for object classification with a detection focus on small objects. The image may be a frontal or profile facial image, processed end to end. The model identifies and localizes different types of acne. Instances are counted and visualized such as by annotating the source image. An example annotation is an overlay identifying a type and location of each instance. Counts by acne type assist with scoring. A product and/or service may be recommended in response to the identification of the acne (e.g. the type, localization, counting and/or a score).

15 Claims, 6 Drawing Sheets

(52) U.S. Cl.
CPC ............... *G06T 2207/20084* (2013.01); *G06T 2207/30088* (2013.01); *G06T 2207/30201* (2013.01)

(56) References Cited

FOREIGN PATENT DOCUMENTS

| KR | 10-2160128 B1 | 9/2020 | | |
|---|---|---|---|---|
| WO | WO-2019037014 A1 | * | 2/2019 | ............... G06T 5/00 |

OTHER PUBLICATIONS

Written Opinion and Preliminary Search Report mailed Oct. 12, 2020 in French Application No. 2013002.
Shen et al., "An Automatic Diagnosis Method of Facial Acne Vulgaris Based on Convolutional Neural Network", www.nature.com/scientificreports, Apr. 11, 2018.
Janayed et al., "AcneNet—A Deep CNN Based Classification Approach for Acne Classes", 12th International Conference on Information & Communication Technology and System (ICTS) Jul. 18, 2019, pp. 203-208.
Redmon et al., "YOLOv3: An Incremental Improvement", Apr. 8, 2018.
He et al., "Deep Residual Learning for Image Recognition", Dec. 10, 2015.
Preliminary Search Report issued Aug. 23, 2021, in corresponding France Patent Application No. 2013002 (with English Translation of Category of Cited Documents), 11 pages.
Rashataprucksa Kuladech et al., "Acne Detection with Deep Neural Networks", 2020 2nd International Conference On Image Processing And Machine Vision, Aug. 5, 2020, pp. 53-56, XP055832085, Extrait de !'Internet: URL:http://dx.doi.org/10.1145/3421558.3421566.
Hang: "Assessing the Severity of Acne via Cell Phone Selfie Images Using A Deep Learning Model", CSE Developer Blog, Feb. 5, 2019, pp. 1-12, XP055757159, Extrait de !'Internet: URL: https://devblogs.microsoft.com/cse/201 9/02/05/assessing-the-severity-of-acne-via-cell-phone-selfie-images-using-a-deep-learn in g-model/.
Baum, S., "Dermatology entrepreneurs develop app to analyze acne selfies, customize treatment", MedCityNews, May 31, 2016, URL: https://medcitynews.com/2016/05/dermatology-entrepreneurs-develop-app-analyze-acne-selfies-customize-treatment/?rf=1 [Retrieved on Jul. 5, 2024], 7 pages.
Seller, D., "MD Acne CEO Says Apple's Carekit is a Game Changer", Apple World Today, Sep. 14, 2016, URL: https://www.appleworld.today/2016/09/14/md-acne-ceo-says-apples-carekit-is-a-game-changer/ [Retrieved on Jun. 6, 2022], 11 pages.
Shacklett, M., "How an analytics app is changing the lives of acne patients", Tech Republic, Dec. 6, 2016, URL: https://web.archive.org/web/20161210175411/https://www.techrepublic.com/article/how-an-analytics-app-is-changing-the-lives-of-acne-patients/ [Retrieved on Mar. 26, 2024], 6 pages.
Weiner, Z., "This App Is Trying To Change The Way We Treat Acne", Bustle, Mar. 17, 2017, URL: https://www.bustle.com/p/this-app-is-trying-to-treat-acne-without-having-to-step-into-a-doctors-office-44897 [Retrieved on Oct. 9, 2023], 4 pages.
"MDacne—uses mobile image analysis and artificial intelligence to disrupt physician centric Acne treatment", Medgadget, Jul. 30, 2016, URL: https://www.medgadget.com/2016/07/mdacne-uses-mobile-image-analysis-and-artificial-intelligence-to-disrupt-physician-centric-acne-treatment.html [Retrieved on Oct. 9, 2023], 3 pages.
Leichman, A.K., "Say Bye-Bye to Zits Without a Dermatologist Appointment", Israel21c, Aug. 11, 2016, URL: https://www.israel21c.org/say-bye-bye-to-zits-without-a-dermatologist-appointment/ [Retrieved on Oct. 9, 2023], 4 pages.
Strane, M., "MDAcne: A New Way of Treating Acne", The Teen Magazine, Mar. 14, 2018, URL: https://www.theteenmagazine.com/mdacne-a-new-way-of-treating-acne [Retrieved on Oct. 9, 2023], 6 pages.
Solomon, S., "Phone app seeks to bust acne using selfies and algorithms", The Times of Israel, Jun. 14, 2016, URL: https://www.timesofisrael.com/phone-app-seeks-to-bust-acne-using-selfies-and-algorithms/ [Retrieved on Oct. 9, 2023], 3 pages.
"Apple features MDacne—Artificial Intelligence Image Analysis App—on its CareKit blog", Health Tech Newswires, Sep. 6, 2016, URL: https://healthtechnewswires.com/2016/09/06/apple-features-mdacne-artificial-intelligence-image-analysis-app-carekit-blog/ [Retrieved on Oct. 9, 2023], 4 pages.
Kodra, A., "MDacne uses mobile machine learning to offer customized skin care plans", Medium, Jun. 12, 2019, URL: https://medium.com/@austin_32493/mdacne-uses-mobile-machine-learning-to-offer-customized-skin-care-plans-dd3330d54191 [Retrieved on Oct. 9, 2023], 6 pages.
"Words starting with "focus"—All dictionaries", goo Dictionary, URL: https://dictionary.goo.ne.jp/word/%e7%84%a6%e7%82%b9/] [Retrieved on Feb. 16, 2024], (with unedited computer-generated English translation), 6 pages.
"The meaning, usage and pronunciation of focus", Eijiro on the Web, URL: https://eow.alc.co.jp/search?q=focus [Retrieved on Feb. 16, 2024], (with unedited computer-generated English translation), 12 pages.
"Terminology Wiki", CVML Expert Guide, URL: https://cvml-expertguide.net/terms [Retrieved on Feb. 16, 2024], (with unedited computer-generated English translation), 13 pages.
"A thorough explanation of the YOLO series, a representative algorithm for object detection! [AI paper commentary]", DeepSquare Media, Sep. 19, 2020, (with unedited computer-generated English translation), 18 pages.

* cited by examiner

SYSTEMS AND METHODS FOR ACNE COUNTING, LOCALIZATION AND VISUALIZATION

CROSS-REFERENCE TO RELATED APPLICATION

This application claims the benefit of priority from U.S. Provisional Application No. 63/086,694 filed Oct. 2, 2020, and claims the benefit of priority from French Application No. FR 2013002 filed Dec. 10, 2020, the entire contents of each of which are incorporated herein by reference.

FIELD

This application relates to the areas of computer image processing, convolutional neural networks and dermatology and more particularly to systems and methods for acne counting, localization and visualization and to e-commerce systems and methods utilizing same.

BACKGROUND

Skin conditions such as acne often affect the face and other areas of the body may also present such conditions. In the case or acne, oil or dead skin cells plug a follicle causing blemishes of various types. Though common among teens, it also occurs in people of other age groups. Given a facial image, an acne localization task aims to detect whether any acne is present in the facial portrait.

Acne localization is useful in downstream applications related to dermatology and image visualization.

SUMMARY

Systems, methods and techniques are provided for acne localization, counting and visualization in accordance with embodiments. An image is processed using a model to identify (classify) objects. In an embodiment, the model is a convolutional neural network (CNN) configured for object classification having a detection focus on small objects. In an embodiment, the image is a facial image, in frontal or profile mode processed end to end by the CNN, without cropping. In an embodiment, the model identifies and localizes different types of acne. Acne instances are counted (e.g. by type) and visualized such as by annotating the source image. An example annotation is an overlay identifying a type and location of each instance. Counts by acne type assist with scoring. In an embodiment, a product and/or service may be recommended in response to the identification of the acne (e.g. the type, localization, counting and/or a score). In an embodiment, purchase is facilitated.

In an embodiment, there is provided a method comprising: analyzing a source image to determine respective locations of instances of acne; and visualizing the instances of acne on the source image for display; wherein the source image is analyzed using a model configured to: detect at least one type of acne in images; and focus detection on small objects in images.

In an embodiment, the model is a deep learning neural network model configured for object classification and localization.

In an embodiment, the model is configured to process the image on a pixel level, operating end-to-end to directly detect acne location without cropping the source image.

In an embodiment, the model generates respective anchor boxes providing location information for each of the instances of acne detected.

In an embodiment, an anchor box aspect ratio, for use to define one of the anchor boxes, is calculated using k-means clustering from acne instances identified in a dataset of images.

In an embodiment, the model is patch-based and the method comprises providing patches of skin from the source image to the model for processing to detect instances of acne.

In an embodiment, the model is patch-based and the method comprises providing patches of skin from the source image to the model for processing to detect instances of acne, and wherein the patches are determined in accordance with a skin mask.

In an embodiment, visualizing the instances of the acne indicates a respective location for each of the instances on the source image.

In an embodiment, visualizing the acne indicates a respective type of acne for each of the instances on the source image.

In an embodiment, the at least one type of acne includes one or more of retentional acne, inflammatory acne and pigmentary acne.

In an embodiment, the method comprises determining a count of the instances of acne.

In an embodiment, the method comprises obtaining a recommendation for a product and/or a service specific to treat the instances of the acne.

In an embodiment, the method comprises communicating with an e-commerce system to purchase the product and/or service.

In an embodiment, the source image comprises a facial image in frontal mode or profile mode.

In an embodiment, the method comprises acquiring the source image.

In an embodiment, there is provided a method comprising: analyzing a source image to determine respective locations of instances of acne; and generating and providing an acne score responsive to a count of the instances; wherein the source image is analyzed using a model configured to: focus detection on small objects in images; and detect at least one type of acne in images.

In an embodiment, the acne score is responsive to one or more of location, count, and type of acne.

In an embodiment, the method comprises comprising generating a recommendation for one or more of a product and a service specific to treat the instances of acne.

In an embodiment, the recommendation is generated in response to factors selected from the group: acne type, count by type, score by type, location of the acne, location of purchaser, delivery location, regulatory requirement, counter indication, gender, co-recommendation, likelihood of user to follow use guidelines, and likelihood of user to follow use guidelines.

In an embodiment, the method comprises comprising visualizing the instances of acne on the source image.

In an embodiment, there is provided a computing device comprising circuitry configured to perform a method according to any one of the embodiments.

In an embodiment, there is provided a computing system comprising circuitry configured to provide: an interface to receive a source image and return an annotated source image which visualizes instances of acne determined by a model configured to process the source image; wherein the model is configured to: focus detection on small objects in images; and detect at least one type of acne in images.

In an embodiment, the computing system is configured to provide: a recommendation component configured to recommend a product and/or service to specifically treat at least some of the instances of acne; and, an e-commerce transaction component to facilitate a purchase of the product and/or service.

In an embodiment, the model comprises one of: a patch-based model configured to receive patches of skin from the source image for processing to detect instances of acne, the patches determined in accordance with a skin mask; and a single detection layer model configured to output a plurality of predictions comprising a three dimensional tensor encoding bounding box, objectness, and class predictions, and wherein the plurality of predictions are filtered to filter redundant detections on a same acne instance.

DETAILED DESCRIPTION

In accordance with an embodiment, there is shown and described a model configured to process a source image to detect instances of acne. The model is configured to determine respective locations for the instances of acne, performing an acne localization task. In an embodiment, the model is configured to return bounding boxes or coordinates. In an embodiment, the model is also configured to classify the instances to particular types of acne. In an embodiment the source image is a full facial image.

In an embodiment, the model is a deep learning model. In an embodiment, the model has a focus on small objects.

In an embodiment, the model is end-to-end and operates on a pixel-level, meaning the model processes an entire image (e.g. of a face) and directly makes detections of acne on the image without any cropping.

In the following description, various embodiments of a model for processing source images are described, where a first group of embodiments ("first model embodiments" of a "first model type") are based upon a modified YOLO object detection deep learning network and a second group of embodiments ("second model embodiments" of a "second model type") are based on a patch based deep learning network. (See J. Redmon and A. Farhadi, YOLOv3: An Incremental Improvement, arXiv:1804.02767, Apr. 8, 2018 URL: arxiv.org/abs/1804.02767, incorporated herein by reference where permissible and hereinafter "YOLOv3").

It will be understood that various features described in association with an embodiment of one of the model types are applicable to an embodiment of the second model type. By way of example, but without limitation, localization of acne, detection by acne type, acne counting (e.g. by type), and acne visualization features are applicable to both model types. In embodiments, the first and second model embodiments are useful to process a full facial image, whether a frontal or profile image, without cropping. In embodiments, the first and second model embodiments are useful to process a full facial image as guided by a skin mask generated from the face image. While some of these features relate to the operations of the embodiments of the models themselves such as acne detection features (e.g. localization and classification), other features such as counting, visualization etc. are operations associate with processing output from a model. These and other features are common between the model embodiments.

First Model Embodiments

Figure 1B:
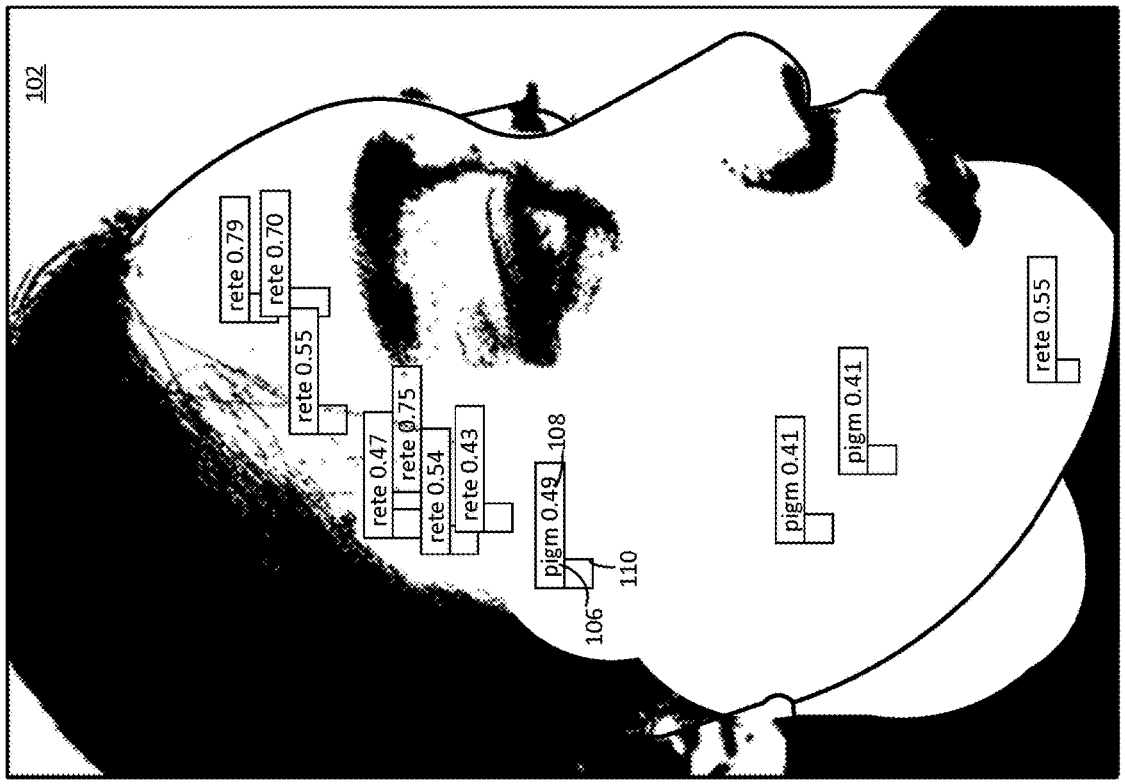
FIGS. 1A, 1B and 1C are facial images annotated using visualization to show instances of acne by type and location, in accordance with an embodiment.
Figure 1A:
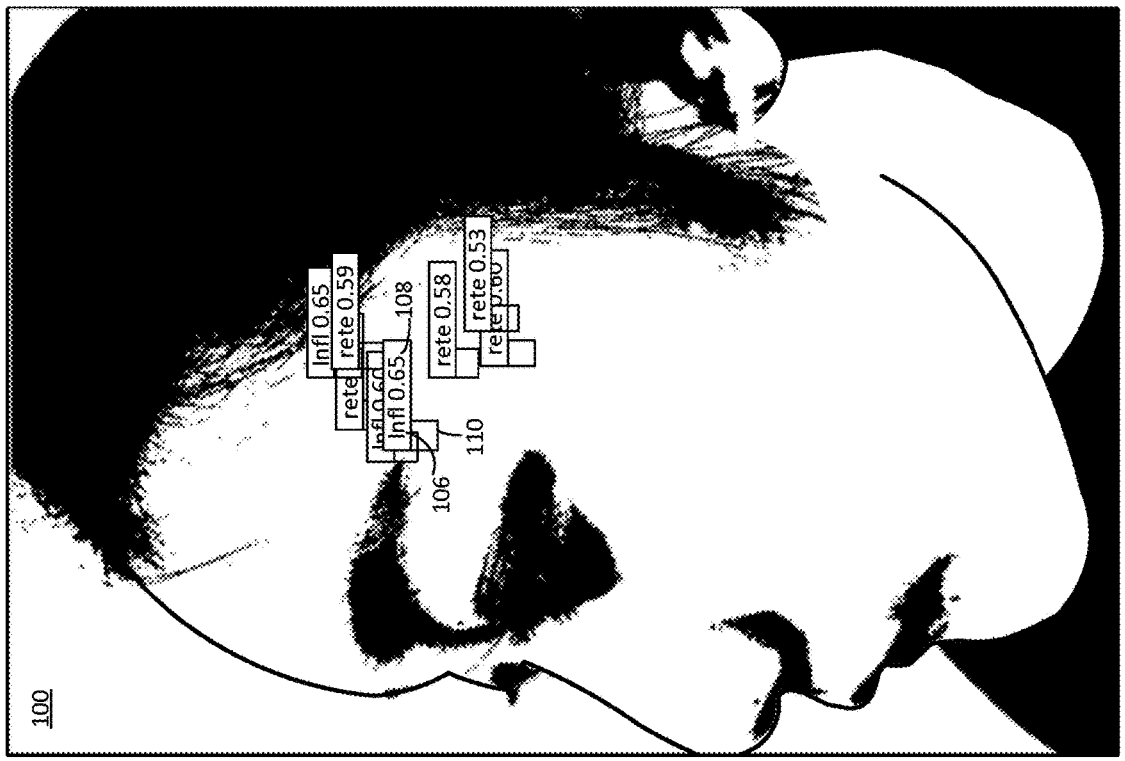
Figure 1C:
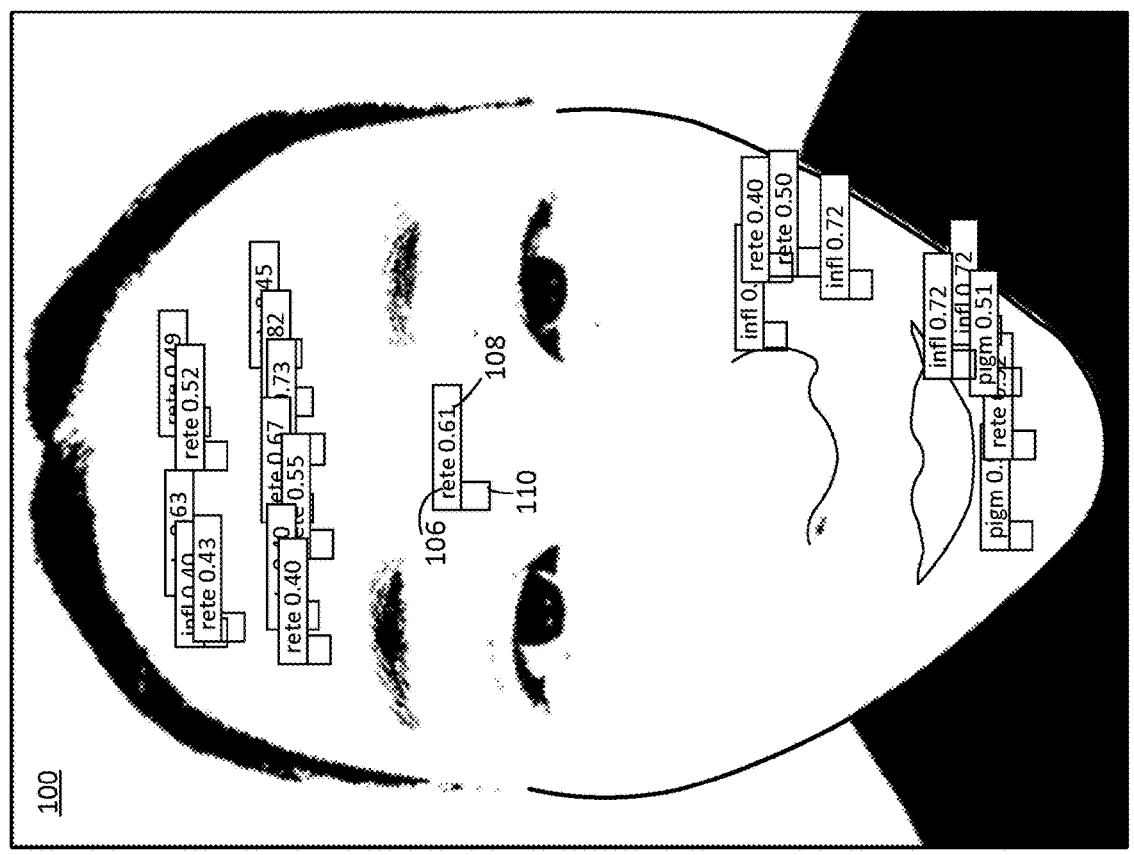

FIGS. 1A, 1B and 1C show examples of acne visualization following analysis of respective source images using the model, in accordance with an embodiment, where three types of acne are detected and visualized. The types include retentional acne, inflammatory acne and pigmentary acne. The types of acne that can be detected depend on the training data used when training the model. This means the model itself has expandability to learn and detect other types of acne if applicable training data is provided. It is understood, that in an embodiment, fewer types of acne may be trained for detection.

As shown, in accordance with an embodiment, the model also supports acne detection on three facial views (left profile/side, right profile/side and frontal modes) of the input. The model, in this embodiment, is viewpoint invariant and may process images from any of the viewpoints/modes.

FIGS. 1A, 1B and 1C are black and white (BW) simulated images 100, 102 and 104 showing annotated source images visualizing acne instances, in accordance with an embodiment. The images 100, 102 and 104 are converted from original color images and edited for patent application compliance purposes, though color images are used, in the embodiment, in practice such as to present a truer image of the subject. Image 100 is a left side (profile) view, image 102 is a right side (profile) view and image 104 is a frontal view.

In the embodiment, the three-view annotation intentionally focuses on specific parts of the face on each view. For the example, the frontal view 104 annotates acne around mouth and in the center of the image because they are more visible in this view. Similarly, the side views 100 and 102 annotate acne around temples where frontal view 104 does not. In the embodiment, the training data is defined (labeled) in such a manner for the respective views and the model is trained to identify data in respect of such locations accordingly.

In the embodiment, instances are labeled with a type 106, a detection confidence measure (e.g. a numerical value) 108 and a bounding box 110. Acne may be closely adjacent in a human face and as such the labels may overlap when visualized at a particular scale. In an embodiment, (though not shown in the BW examples), acne type may be distinguished using different colors for the labels or through other means. Other label types may be used (e.g. color coded bounding boxes without text), etc. In the present example, the acne type is depicted as "infl" (inflammatory), "rete" (retentional) and "pigm" (pigmentation). In terms of the detection confidence measure, the value is on a scale of 0 to 1 such that a measure of 0.58 represents a confidence of 58% that the detected instance is acne. In the embodiment, further filtering is used to select among the detected instances of acne for visualization. For example, a threshold of 50% is used to visualize instances at or above the threshold. The threshold may be varied.

First Model Type Structure

In an embodiment, the main architecture of the model is based on YOLOv3 object detection algorithm.

Bounding Box Prediction (Location)

In brief, YOLOv3 predicts bounding boxes using dimension clusters as anchor boxes, predicting four coordinates ($t_x$, $t_y$, $t_h$, $t_w$) for each bounding box (e.g. sometimes referenced herein as "bbox"). A box may be offset from a top left corner of the image by ($c_x$, $c_y$). The width and height of the box is predicted as offsets from cluster centroids ($\sigma(t_x)$, $\sigma(t_y)$). Centre coordinates of the box are predicted relative to the location of filter application using a sigmoid function. Sum squared error loss is used during training.

YOLOv3 describes predicting an objectness score for each bounding box using logistic regression. A score should be 1 if the bounding box prior overlaps a ground truth object by more than any other bounding box prior. If the bounding box prior is not the best but does overlap a ground truth object by more than some threshold the prediction is ignored, using a threshold of 0.5. One bounding box prior is assigned in YOLOv3 for each ground truth object. If a bounding box prior is not assigned to a ground truth object it incurs no loss for coordinate or class predictions, only objectness.

Class Prediction (e.g. Object Prediction or Acne by Type)

Multi-label classification is used for class prediction for each box via independent logistic classifiers. Class predictions are trained using binary cross-entropy loss.

YOLOv3 describes box predictions across three scales. From a base feature extractor several convolutional layers are added. The last of such predicts a 3-d tensor encoding bounding box, objectness, and class predictions. Accordingly, for 3 boxes at each scale, the tensor is N×N×[3*(4+1+80)] for the 4 bounding box offsets, 1 objectness prediction, and 80 class predictions.

Then, the feature map from 2 layers previous is upsampled by 2× and an earlier feature map is merged with the upsampled features using concatenation. A few more convolutional layers are added to process the combined feature map. A similar tensor is predicted at twice the size. A similar approach is used again to predict a third tensor for the third scale, combining the prior computation as well as fine grained features from earlier processing. k-means clustering is used to determine the bounding box priors where 9 clusters and 3 scales are chosen arbitrarily and the clusters are divide up evenly across scales.

The backbone net for feature extraction described in YOLOv3 is a 53 layer convolutional network named DARKNET-53.

Modification

In accordance with an embodiment herein, the model disclosed in YOLOv3 is modified to focus on smaller objects by:
  Reducing the size of the backbone net;
  Retaining only one YOLO detection layer and recalculating the anchor box size (aspect ratio) and
  Fine-tuning the model to the best performance on the training dataset for the present task of acne localization.

In retaining only one YOLO detection layer, prediction is performed at one scale level in the embodiment. Thus, in the embodiment, the YOLO detection layer is the layer that handles prediction of bounding boxes. It receives a feature (e.g. output of the backbone net layers) and outputs objectness, class prediction and bbox location. The layer itself does not have a limit on the number of predictions. In an embodiment, during inference, the layer will output a large number of predicted boxes. These are filtered using non-maximum suppression (NMS) with a manually set confidence threshold.

In the embodiment, filtering using NMS is directed, at least in part to filter redundant detections on the same acne instance. When the model predicts two or more boxes on the same acne, NMS filters out the instances with lower confidence and preserve the highest confidence box on the specific instance.

In an embodiment, the model is trained to predict three classes of objects for the respective 3 acne types. There is no additional or background class because YOLO does not make background predictions (e.g. YOLOv3 doesn't draw a bounding box on background and indicate that it's background. YOLOv3 only predicts the target classes). The number and types of classes can be easily adjusted to suit the format of the data. For example, if more classes of objects (e.g. acne or other objects) were identified in the data, the model could be adjusted and trained to predict more classes.

With respect to tuning, in an embodiment, various operations were performed including: 1) intensive data augmentation comprising: converting images to HSV color space and adding random color jittering (randomly change the value within a range) on the Saturation and Value channels; and random affine transformation on the image; 2) Using a multi-step learning rate scheduler; and 3) using an evolution algorithm to evolve the hyper-parameters from the above augmentations by training multiple rounds and iteratively selecting the best setup.

In an embodiment, as described in YOLOv3, the anchor box aspect ratio is calculated using k-means clustering of acne instances identified in the (training) image dataset (e.g. as annotated by a human reviewer (e.g. an expert). That is the anchor boxes are clustered in terms of the aspect ratio using k-means clustering operations. Anchor boxes are used for guiding bounding box prediction in YOLOv3. In other approaches, operations may find a patch of the image that potentially contains the target object then predict a bounding box around the object. But this is quite a computationally demanding task.

Understanding in the art developed such that it was determined that it was not necessary to predict a raw box because the dataset should have some intrinsic characteristics. By way of example, a car dataset should always have long rectangular bbox and a face dataset should have near square bbox. Using these principles, the image dataset is evaluated to cluster the size of the bbox and find some common sizes that are shared. Those sizes are used as anchor boxes. The model then only needs to predict the offset from the anchor box and it saves much computational work. In an embodiment, the algorithm used follows the same approach. The algorithm first obtains all of the bounding boxes from the training annotation, extracts and formats the boxes as (width, height) data pairs, and then use k-means (a clustering technique to divide data into k individual clusters) to find the cluster centroids. The number of clusters (k) is manually set, and it should be consistent with the YOLO layer which takes in a certain number of anchor boxes. In an embodiment, k=5 for the model.

Table 1 shows a model structure by layer, in accordance with an embodiment, following the modifications thus described.

TABLE 1

| Layer | Type | Filters | Size/Stride | Input | Output |
|---|---|---|---|---|---|
| 0 | Convolutional | 16 | 3 × 3/1 | 1024 × 1024 × 3 | 1024 × 1024 × 16 |
| 1 | Maxpool | | 2 × 2/2 | 1024 ×1024 × 16 | 512 × 512 × 16 |
| 2 | Convolutional | 32 | 3 × 3/1 | 512 × 512 × 16 | 512 × 512 × 32 |
| 3 | Maxpool | | 2 × 2/2 | 512 × 512 × 32 | 256 × 256 × 32 |
| 4 | Convolutional | 64 | 3 × 3/1 | 256 × 256 × 32 | 256 × 256 × 64 |
| 5 | Maxpool | | 2 × 2/2 | 256 × 256 × 64 | 128 × 128 × 64 |
| 6 | Convolutional | 128 | 3 × 3/1 | 128 × 128 × 64 | 128 × 128 × 128 |
| 7 | Maxpool | | 2 × 2/2 | 128 × 128 × 128 | 64 × 64 × 128 |
| 8 | Convolutional | 256 | 3 × 3/1 | 64 × 64 × 128 | 64 × 64 × 256 |
| 9 | Maxpool | | 2 × 2/2 | 64 × 64 × 256 | 32 × 32 × 256 |
| 10 | Convolutional | 512 | 3 × 3/1 | 32 × 32 × 256 | 32 × 32 × 512 |
| 11 | Maxpool | | 2 × 2/1 | 32 × 32 × 512 | 32 × 32 × 512 |
| 12 | Convolutional | 1024 | 3 × 3/1 | 32 × 32 × 512 | 32 × 32 × 1024 |
| 13 | Convolutional | 128 | 1 × 1/1 | 32 × 32 × 1024 | 32 × 32 × 128 |
| 14 | Upsample | | 2 × 2/1 | 32 × 32 × 128 | 64 × 64 × 128 |
| 15 | Shortcut (14, 8) | | Concatenate layer 14 and 8 outputs | | |
| 16 | Convolutional | 256 | 3 × 3/1 | 64 × 64 × 384 | 64 × 64 × 256 |
| 17 | Convolutional | 24 | 1 × 1/1 | 64 × 64 × 256 | 64 × 64 × 24 |
| 18 | YOLO | | | | |

A model per se, does not predict a total count of the instances of objects (e.g. acne) by class or in the aggregate directly. Thus, a count by class or aggregate may be determined by respectively counting up the instances of acne by class from the model's predictions (output), for example, after filtering the predictions such as by using non-maximum suppression.

A comparison of the count determined from predictions with a count made of the ground truths may be used to evaluate the model. Common object detection metrics depend on how one defines what counts as a hit and a miss. Often a threshold of ratio of overlap (Intersection over Union) is used but this threshold can be arbitrarily set high or low, affecting the accuracy numbers significantly.

In an embodiment, counts are generated and used as a way of evaluating how well the model is working.

In an embodiment, counts are generated from inference time use of the model for use in downstream tasks. Instead of (or in addition to) predicting the precise locations of acne, an API for the model can be configured to determine counts. Downstream applications can use counts or even scores that are based on predicted counts for tasks like skin condition severity estimation, product and/or service recommendation, etc.

Dataset

A facial image dataset that contains 348 facial images of 116 different subjects (3 views per subject) was collected. A group of dermatologists labeled the images and identified any visible acne that may belong to any of the three types: inflammatory acne, retentional acne, and pigmentary acne.

The identified acne was then saved in the format of coordinate of the centre point for defining ground truths for training and testing, etc.

In an embodiment, a group of three dermatologists (experts) reviewed and annotated an image set. Each expert annotated all the images and identified all three types of acne. In an embodiment, the annotated data (the three versions of annotation) was merged in accordance with the following steps:

Merge all three versions. The total number of boxes after this step is the simple addition of those of the three original annotation.

Filter redundant boxes based on a similar logic as NMS. I.e. if the IoU (intersection over union) of two boxes is larger than certain threshold, use the larger box as groundtruth (GT). If multiple boxes overlap each other and all have large IoU, use the largest box as the GT.

Evaluation

The performance of acne localization was measured based on common object detection metrics. It includes Precision (P), Recall (R), mAP and F1 score. Note that mAP and F1 score are direct formulations based on Precision and Recall. Performance evaluation for the localization task is shown in Table 2.

TABLE 2

| Class | Images | Targets | P | R | mAP | F1 |
|---|---|---|---|---|---|---|
| all | 69 | 1860 | 0.225 | 0.568 | 0.313 | 0.322 |
| pigm | 69 | 796 | 0.233 | 0.531 | 0.267 | 0.324 |
| infl | 69 | 275 | 0.246 | 0.636 | 0.443 | 0.355 |
| rete | 69 | 784 | 0.197 | 0.536 | 0.23 | 0.288 |

The following abbreviations for three types of acne evaluated in the current model are used in Table 2: pigm=pigmentation, infl=inflammation, rete=retentional and where P=Precision, R=Recall.

The same model is evaluated in respect of the counting task as well and the results are shown as follows in Table 3:

TABLE 3

| | Pigmentation | Inflammatory | Retentional |
|---|---|---|---|
| <5 Percentage | 0.50725 | 0.82609 | 0.56522 |
| error by class | 6.058 | 2.4638 | 5.2319 |
| Average error | 4.584541063 | | |

The error calculated is absolute error (|#Predicted−#GroundTrue|). The metrics evaluated against are <5 Percentage (i.e. what ratio of the test cases show an absolute error <5?), error by class and average error of all classes.

Though the above embodiments are describe in relation to processing an entire facial image, in an embodiment, a skin mask may be defined, for example, using facial landmarks, to indicate portions of the image that depict skin. The above first model embodiments may process the skin portions of facial image as directed by the skin mask.

In an embodiment, operations may reject an image that does not include a face and not process the image for acne localization and count. In an embodiment, for example, operations may process the image to locate facial landmarks are reject or further process the image accordingly.

Second Model Embodiments—Patch-Based Acne Localization

A possible drawback with the Yolo-based approach of the first embodiments above is that noisy annotations can lead to weak results. Therefore, provided herein are second model embodiments in accordance with a patch-based approach that localizes acne spots. In an embodiment, a patch based approach is applied to an entire face image. In an embodiment, a patch based approach is applied using a skin mask to process one or more portions of the face image.

Figure 2:
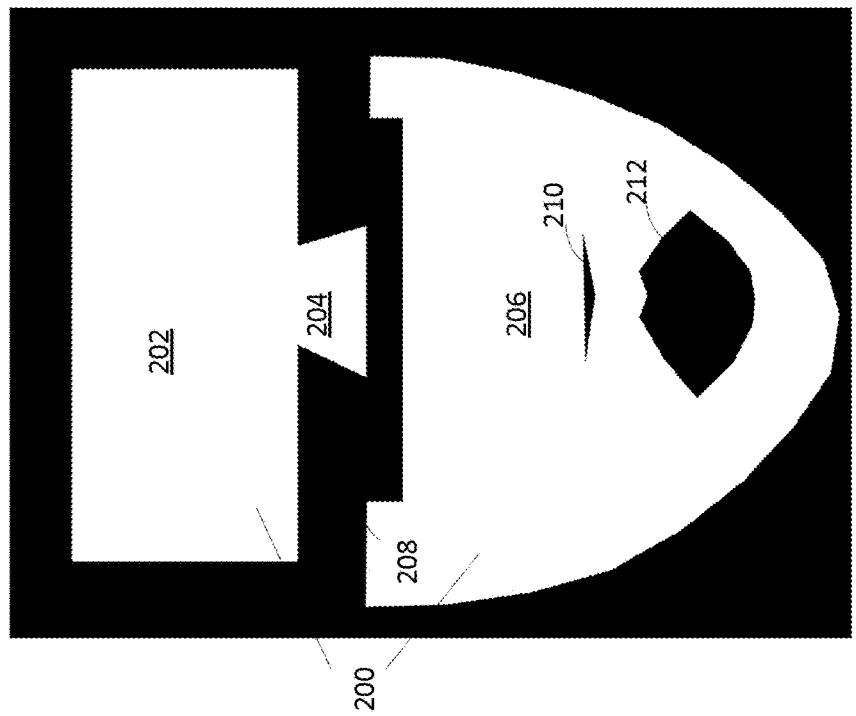
FIG. 2 is an illustration of an example of a skin mask based on facial landmarks for use when processing a facial image in accordance with an embodiment.

For example, in a mask directed embodiment, at inference time, a source image of a face (e.g. a selfie image) is pre-processed by a facial landmarks detector to define a skin mask for the face. An example of a skin mask 200 based on the landmarks is shown in FIG. 2 where mask portions are white and show regions for processing for acne and non-mask portions are black showing regions that are not processed. In the present example, mask 200 shows an upper face component 202 for the forehead, a T-line component 204 over the nose bridge, and a lower face component 206 for the cheeks, jaw line and chin, where portions are omitted for an eye region (e.g. 208), a lower nose region 210 and a lip region 212. Background around the face is also omitted from the mask.

At inference time, in the mask related embodiment, patches of resolution are created within the generated skin mask by scanning from top-left to bottom-right, with a stride of one third (⅓) patch width. Patch width is normalized by defining it as a width of the face divided by 15. Each patch is passed through a trained convolutional neural network (i.e. a second model embodiment) described below. In an embodiment, the model outputs a list of probabilities of the following classes: inflammatory, retentional, pigmented (three acne types or classes) and healthy skin. In an embodiment, non-maximum Suppression (NMS) is applied to select the best boxes among the returned detected acne candidates.

In a non-mask related embodiment, similar operations are performed using patches to process the entire facial image, for example, including non-skin portions such as background, hair, eyes and lips. For example, at inference time, in the non-mask related embodiment, patches of resolution are created within the entire image by scanning from top-left to bottom-right, with a stride of one third (⅓) patch width as described. Each patch is passed through a trained convolutional neural network (i.e. a second model embodiment) described below. In an embodiment, the model outputs a list of probabilities of the following classes: inflammatory, retentional, pigmented (three acne types or classes) and healthy skin. In an embodiment, non-maximum Suppression (NMS) is applied to select the best boxes among the returned detected acne candidates. The healthy skin class gives the classifier an option other than one of three acne classes.

In an embodiment, the selected boxes are useful to perform an acne count, and using the source image, an acne visualization. In an embodiment, a filter is applied to select between those instances of the best boxes of detected acne using a threshold confidence measure. For example, detected instances at or above the threshold (or only those above the threshold) are counted and/or visualized.

Figure 3:
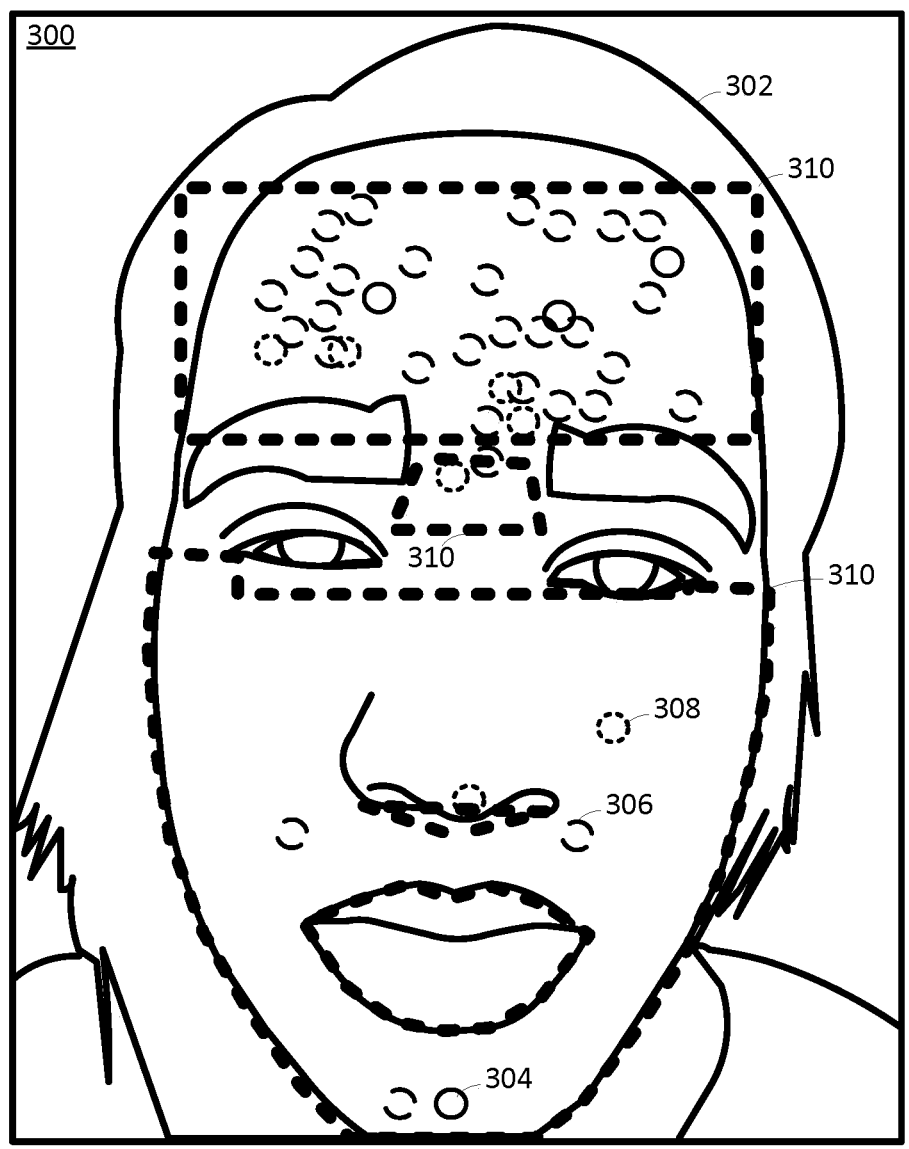
FIG. 3 is an illustration of a facial image with acne visualization and mask visualization in accordance with an embodiment.

In accordance with an embodiment, FIG. 3 is an illustration of a screen shot 300 showing a source facial image 302 that is annotated to visualize acne (e.g. 304, 306 and 308). Screen shot 300 also shows the source image annotated to show the applicable skin mask 310 (here, outlined with a broken line) determined for the face. In FIG. 3, the acne is visualized using circles about a center point of the box of each detected instance of acne that is to be visualized. In an embodiment, in practice, the circles are different colors or different grayscale values to distinguish the 3 acne classes. In the present illustration the circles are distinguished using an unbroken line style (e.g. 304) or one of two broken line styles (e.g. 306, and 308). In an embodiment, the skin mask is not visualized (not shown). The skin mask may not be visualized as one was not used or because it was used but it is not desired to be shown.

Second Model Type Structure and Training

In an embodiment, a patch-based model comprises a residual network backbone (for example, ResNet-50, having 50 neural network layers) and three fully connected layers where a rectified linear activation function (e.g. LeakyReLU (Leaky Rectified Linear Unit)) is interleaved between adjacent fully connected (FC) layers. The final layers appear as FC1→LeakyRelu1→FC2→LeakyRelu2→FC3. (See, He, Kaiming; Zhang, Xiangyu; Ren, Shaoqing; Sun, Jian (2015 Dec. 10). "Deep Residual Learning for Image Recognition". arXiv:1512.03385, incorporated herein by reference, where permissible.)

To create a patch-based model dataset, in accordance with an embodiment, 2450 healthy patches and 3577 acne patches (patches including instances of any of the three acne classes previously described herein) were respectively sampled from the full face images of the dataset described above with reference to the first model embodiments. In a training phase, the network is trained with a standard cross entropy loss function, with data augmentation including random affine transformation, random horizontal flip and channel shuffle.

In an embodiment, frontal images were utilized for masking and annotating.

To process a source image to detect instances of acne, by type, in accordance with an embodiment where a mask is used, the source image is processed using landmark detection to define an applicable mask, defining regions of the face having skin for analysis. In accordance with the applicable mask, a plurality of overlapping patches (responsive to patch size and stride) are extracted from the skin image and processed by the model. The model produces a list of probabilities of the following classes: inflammatory, retentional, pigmented (three acne types or classes) and healthy skin. The mask directs operations to ignore any eyes, lips, hair, background in the source image. Multiple detected instances of the same acne are filtered to select a better/best instance (e.g. using NMS). A second filter is applied to select detected instances having at least a minimum confidence level.

Similarly as described with reference to embodiments of the first model, in an embodiment using a second model type, detected instances of acne by type are counted. In an embodiment, a score is computed. In an embodiment, detected acne is visualized in association with a source image. In an embodiment, the mask is visualized in association with the source image, showing which regions of the skin were processed.

Downstream Applications

The following description relates to any of the first model embodiments and the second model embodiments. Thus, in accordance with the embodiments, analysis operations utilize a model that is configurable to output locations of instances of acne detected in a source image (e.g. of skin such as on a face in frontal or profile mode) where different types of acne (classes of objects) are distinguishable by the model. Analysis or other determination operations can count the instances, for example, to determine an aggregate count and/or a count for each type.

The location, type and/or count define acne data that is useful in downstream applications. In an embodiment, the instances of the acne are visualized on the source image or display using visualizing operations. In an embodiment, the source image is annotated (e.g. using overlays or other techniques) to indicate location. In an example, the location is respective locations for each of the instances on the source image. Visualizing operations, in an embodiment, indicate a respective type of acne for each of the instances on the source image. Visualizing operations, in an embodiment, provide a display of the count.

Acne data (e.g. count and type (classification)) are useful to predict skin condition scores in operations. For example, more retentional acne and less inflammatory acne indicate milder severity and vice versa.

In an embodiment, based on acne data and/or information derived therefrom (e.g. scores) operations recommend products and/or services to target the acne. Operations (e.g. e-commerce operations) facilitate purchasing, in accordance with an embodiment.

In an embodiment, visualizing operations guide application of a product, for example, using the location to indicate where to apply. In an example, the source image is used in the visualizing to provide a user specific tutorial via a graphical user interface (GUI).

Various paradigms and computing systems may be envisioned for practical applications of the model and its output. In an example, a computer network includes at least one client computing device (e.g. for a dermatologist or a consumer) and web-based e-commerce computing system. In the embodiment, the client computing device is enabled to determine instances of acne in a source image and obtain a recommendation for a product and/or service recommendation and to purchase same.

Figure 4:
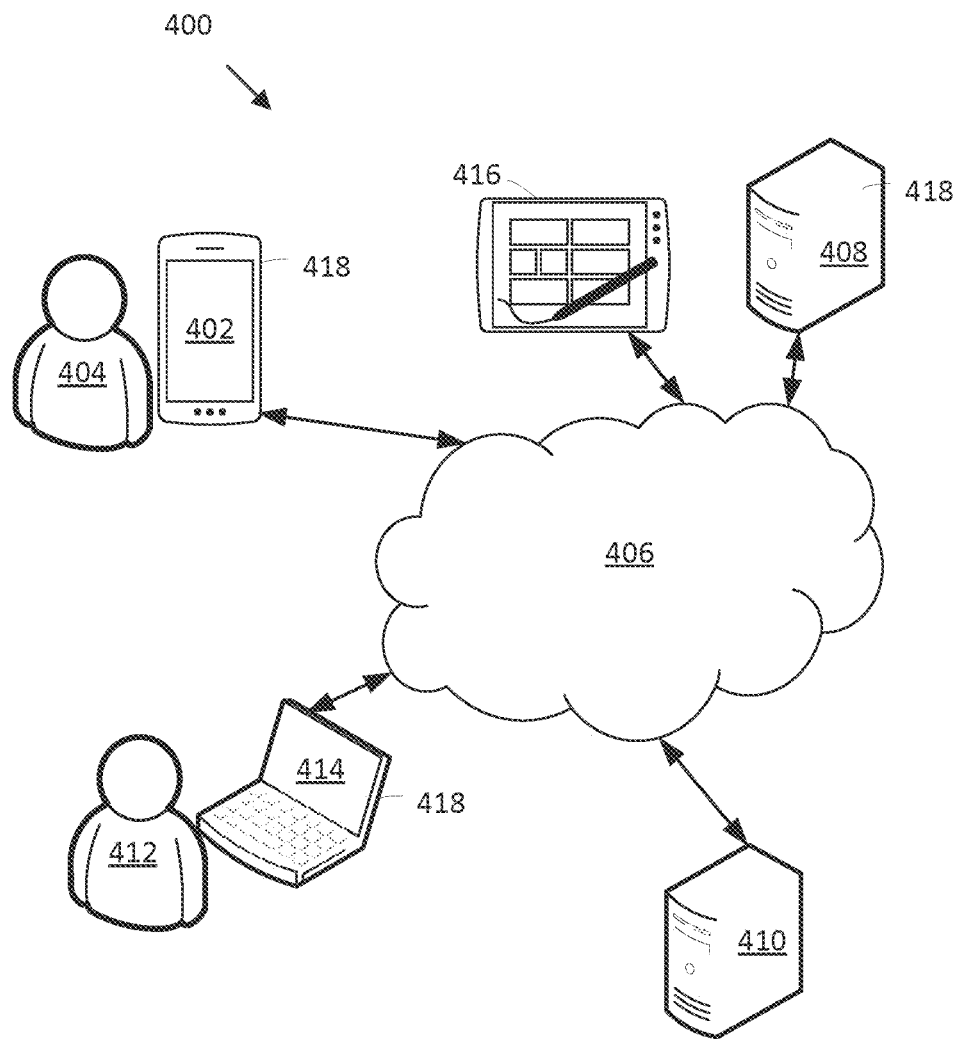
FIG. 4 is an e-commerce network diagram, in accordance with an embodiment, showing a client computing device configured to detect instances of acne in a source facial image and obtain a recommendation for a product and/or service recommendation and to purchase same.

A model for analyzing source images and providing acne data as output may be configured for run-time execution on a user device or on a server or other remote device. An application may be configured to obtain a source image and use the model to generate acne data. The acne data may be used to provide one or more of a diagnosis such as an acne score, a visualization of the acne on the source image and a recommendation for a product or service to specifically treat the acne FIG. 4 is a block diagram of an example computer network 400 in which a computing device 402 for personal use operated by a user 404 is in communication, via a communications network 406, with remotely located server computing devices, namely server 408 and server 410. In an embodiment, the user 404 is a consumer. Also shown is a second user 412 and a second computing device 414 configured for communication via communications network 406. In an embodiment, second user 410 is a dermatologist. In an embodiment, server 408 is configured to provide an instance of the model (418) to process images to generate acne data and a recommendation for a product and/or service to treat acne. Server 408, in an embodiment, generates an acne score and recommendation from acne data received (e.g. without having processed the image itself). In an embodiment, server 408 generates acne data comprising localization data for each instance of detected acne such as for use to visualize the acne. In an embodiment, server 408 generates the visualization such as to provide to another device to display. In an embodiment, server 408 generates acne data comprising a count by type (e.g. without visualization), such as to generate a score.

In an embodiment, server 408 uses rules or a model or other manner to generate recommendations (e.g. recommending a product, a service (which may include a treatment practitioner/service provider or both a product and a service). In an embodiment, respective products are associated to respective treatment plans/use guidelines. In an embodiment recommendations are generated in responsive to factors of acne type, and count or score by type. In an embodiment recommendations are generated in responsive to one or more factors comprising a location of the acne (e.g. on the face), location of purchaser/delivery location, regulatory requirements (e.g. whether a product is available over the counter versus by prescription only), counter indications (e.g. product should not be used while pregnant or prior thereto, not used if certain health conditions are present, not used with other specific product, etc.), gender, co-recommendations (e.g. availability of co-recommended product), likelihood of user to follow use guidelines/treatment plan, and other factors. In an embodiment, an intended user of the product or services completes a user profile (e.g. a questionnaire via a respective user device or such is completed by another (e.g. a dermatologist/treatment practitioner/retail sales staff, etc.) on their behalf for presenting to server 408 to provide data for obtaining recommendations.

In an embodiment server 410 provides an e-commerce interface to purchase products and/or services, for example, such as recommended by server 408.

In an embodiment, computing device 402 is for personal use by the user 404 and is not available to the public. However services from the server are available to the public. Here, the public comprises registered users and/or customers, etc. A computing device 416 available to the public, such as may be located at a brick and mortar store, is also coupled to network 406.

Computing device 402 is configured to perform acne localization, etc. as described herein, namely assessing acne location and determining a count, etc. In the embodiment, a model (CNN) 418 is stored and utilized on board computing device 402. In the embodiment, a second instance of the model 418 is stored at server 408 and provided for use by other computing devices such as via a cloud service, web service, etc. for analysis of image(s) received from a computing device (e.g. 416, etc.).

Computing device 402 is configured to communicate with server 408 for example to provide acne data (which may include score data) and to receive product/service recommendations responsive to the acne data and/or other information regarding the user e.g. age, gender, etc. Computing device 402 (or server 408 on its behalf) is configured to communicate with server 410 to obtain e-commerce services to purchase recommended product(s) and/or service(s).

Computing device 402 is shown as a handheld mobile device (e.g. a smartphone or tablet). However the physical device may be another computing device such as a laptop, desktop, workstation, etc. Acne localization and counting etc. as described herein may be implemented on other computing device types. Computing devices 402, 414 and 416 may be configured using one or more native applications or browser-based applications, for example.

Computing device 402, in the embodiment, comprises a user device, for example, to acquire one or more images such as a picture of skin, particularly a face, and process the one or more images to generate respective acne data, etc. Such activities are referenced as preforming a skin diagnosis. A skin diagnosis may be performed in association with a skin treatment plan where images are acquired periodically and analyzed to determine skin scores such as for acne as described. The scores may be stored (locally, remotely or both) and compared between sessions, for example to show trends, improvement, etc. Skin scores and/or skin images may be accessible to the user 404 of computing device 402 and made available (e.g. via server 408 or communicated (electronically) in another manner via communication network 406) to another user (e.g. second user 412) of computer system 400 such as a dermatologist. Second computing device 414 may also perform skin diagnostics as described. It may receive images from a remote source (e.g. computing device 402, or server 408, etc.) and/or may capture images via an optical sensor (e.g. a camera) coupled thereto or in any other manner. Model 418 may be stored and used from second computing device 414 or from server 408 as described.

An application may be provided to perform the skin diagnostics, suggest one or more products and monitor skin changes following one or more application of the product (which may define treatment sessions in a treatment plan) over a time period. The computer application may provide workflow such as a series of instructive graphical user interfaces (GUIs) and/or other user interfaces, which are typically interactive and receive user input, to perform any of the following activities:

skin diagnostics such as for acne;
product recommendation such as for a treatment plan;
product purchase or other acquisition;
reminding, instructing and/or recording (e.g. logging) product application for respective treatment sessions;
subsequent (e.g. one or more follow up) skin diagnostics; and
present results (e.g. comparative results);
such as in accordance with a treatment plan schedule to monitor progress of a skin treatment plan. Any of these activities may generate data which may be stored remotely for example for user 412 to review, for another individual to review, for aggregation with other user's data (e.g. to aggregately measure treatment plan efficacy), etc.

Comparative results (e.g. before and after results) may be presented via computing device 402 whether during and/or at the completion, etc. of a treatment plan. As noted, aspects of skin diagnostics may be performed on computing device 402 or by a remotely coupled device (e.g. a server in the cloud or another arrangement).

Figure 5:
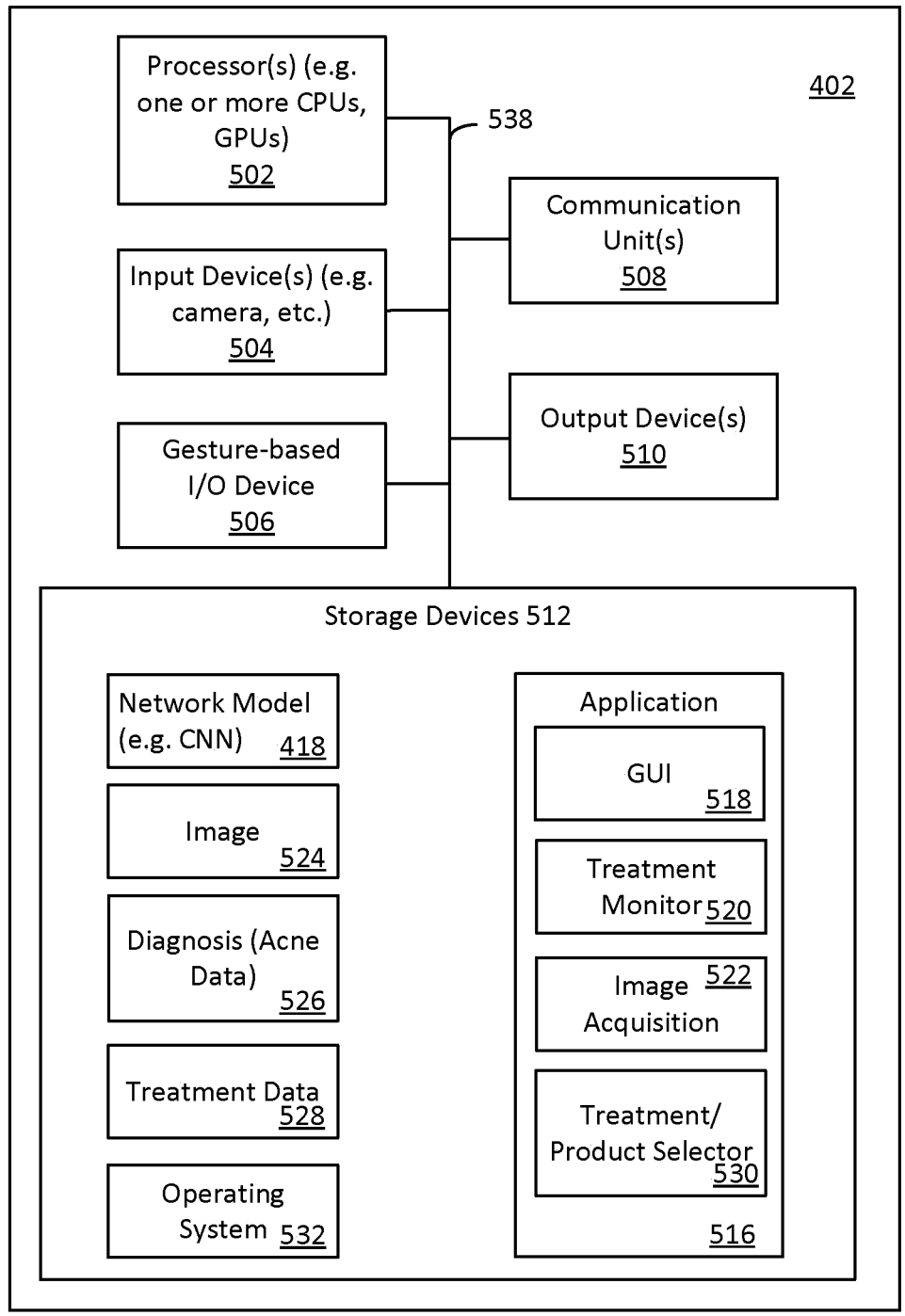
FIG. 5 is a block diagram of a computing device in accordance with an embodiment.

FIG. 5 is a block diagram of computing device 402, in accordance with one or more aspects of the present disclosure. Computing device 402 comprises one or more processors 502, one or more input devices 504, a gesture-based I/O device 506, one or more communication units 508 and one or more output devices 510. Computing device 402 also includes one or more storage devices 512 storing one or more modules and/or data. In an embodiment, modules include model 418, application 516 having components for a graphical user interface (GUI 518) and/or workflow for treatment monitoring (e.g. treatment monitor 520), image acquisition 522 (e.g. an interface) and treatment/product selector 530 (e.g. an interface). Data may include one or more images for processing (e.g. image 524), diagnosis data 526 (e.g. acne data, respective scores, ethnicity, gender or other user data), treatment data 528 such as logging data related to specific treatments, treatment plans with schedules such as for reminders, etc.)

Application 516 provides the functionality to acquire one or more images such as a video and process the images to determine skin diagnosis a deep neural network as provided by model 418.

Storage device(s) 512 may store additional modules such as an operating system 532 and other modules (not shown) including communication modules; graphics processing modules (e.g. for a GPU of processors 502); map module; contacts module; calendar module; photos/gallery module; photo (image/media) editor; media player and/or streaming module; social media applications; browser module; etc. Storage devices may be referenced as storage units herein.

Communication channels 538 may couple each of the components 502, 504, 506, 508, 510, 512, and any modules (e.g. 418 and 516) for inter-component communications, whether communicatively, physically and/or operatively. In some examples, communication channels 338 may include a system bus, a network connection, an inter-process communication data structure, or any other method for communicating data.

The one or more processors 502 may implement functionality and/or execute instructions within computing device 402. For example, processors 502 may be configured to receive instructions and/or data from storage devices 512 to execute the functionality of the modules shown in FIG. 5, among others (e.g. operating system, applications, etc.) Computing device 402 may store data/information to storage devices 512. Some of the functionality is described further herein below. It is understood that operations may not fall exactly within the modules 418 and 516 of FIG. 5 such that one module may assist with the functionality of another.

Computer program code for carrying out operations may be written in any combination of one or more programming languages, e.g., an object oriented programming language such as Java, Smalltalk, C++ or the like, or a conventional procedural programming language, such as the "C" programming language or similar programming languages.

Computing device 402 may generate output for display on a screen of gesture-based I/O device 506 or in some examples, for display by a projector, monitor or other display device. It will be understood that gesture-based I/O device 506 may be configured using a variety of technologies (e.g. in relation to input capabilities: resistive touchscreen, a surface acoustic wave touchscreen, a capacitive touchscreen, a projective capacitance touchscreen, a pressure-sensitive screen, an acoustic pulse recognition touchscreen, or another presence-sensitive screen technology; and in relation to output capabilities: a liquid crystal display (LCD), light emitting diode (LED) display, organic light-emitting diode (OLED) display, dot matrix display, e-ink, or similar monochrome or color display).

In the examples described herein, gesture-based I/O device 506 includes a touchscreen device capable of receiving as input tactile interaction or gestures from a user interacting with the touchscreen. Such gestures may include tap gestures, dragging or swiping gestures, flicking gestures, pausing gestures (e.g. where a user touches a same location of the screen for at least a threshold period of time) where the user touches or points to one or more locations of gesture-based I/O device 506. Gesture-based I/O device 506 and may also include non-tap gestures. Gesture-based I/O device 506 may output or display information, such as graphical user interface, to a user. The gesture-based I/O device 506 may present various applications, functions and capabilities of the computing device 402 including, for example, application 516 to acquire images, view images, process the images and display new images, messaging applications, telephone communications, contact and calendar applications, Web browsing applications, game applications, e-book applications and financial, payment and other applications or functions among others.

Although the present disclosure illustrates and discusses a gesture-based I/O device 506 primarily in the form of a display screen device with I/O capabilities (e.g. touchscreen), other examples of gesture-based I/O devices may be utilized which may detect movement and which may not comprise a screen per se. In such a case, computing device 402 includes a display screen or is coupled to a display apparatus to present new images and GUIs of application 516. Computing device 402 may receive gesture-based input from a track pad/touch pad, one or more cameras, or another presence or gesture sensitive input device, where presence means presence aspects of a user including for example motion of all or part of the user.

One or more communication units 508 may communicate with external devices (e.g. server 408, server 410, second computing device 412) such as for the purposes as described and/or for other purposes (e.g. printing) such as via communications network 404 by transmitting and/or receiving network signals on the one or more networks. The communication units may include various antennae and/or network interface cards, chips (e.g. Global Positioning Satellite (GPS)), etc. for wireless and/or wired communications.

Input devices 504 and output devices 510 may include any of one or more buttons, switches, pointing devices, cameras, a keyboard, a microphone, one or more sensors (e.g. biometric, etc.), a speaker, a bell, one or more lights, a haptic (vibrating) device, etc. One or more of same may be coupled via a universal serial bus (USB) or other communication channel (e.g. 338). A camera (an input device 504) may be front-oriented (i.e. on a same side as) to permit a user to capture image(s) using the camera while looking at the gesture based I/O device 506 to take a "selfie".

The one or more storage devices 512 may take different forms and/or configurations, for example, as short-term memory or long-term memory. Storage devices 512 may be configured for short-term storage of information as volatile memory, which does not retain stored contents when power is removed. Volatile memory examples include random access memory (RAM), dynamic random access memory (DRAM), static random access memory (SRAM), etc. Storage devices 512, in some examples, also include one or more computer-readable storage media, for example, to store larger amounts of information than volatile memory and/or to store such information for long term, retaining information when power is removed. Non-volatile memory examples include magnetic hard discs, optical discs, floppy discs, flash memories, or forms of electrically programmable memory (EPROM) or electrically erasable and programmable (EEPROM) memory.

In an embodiment, as noted, other user oriented computing devices (e.g. 414 and 416) are similarly configured as computing device 402. In an embodiment, for a dermatologist user, application 516 is differently configured, for example, with functionality to work with multiple patients. In an embodiment, for a store located device, application 516 is differently configured, for example, with functionality to work with multiple customers, for store branding, etc.

In another example, network model 418 is remotely located and a computing device (e.g. any of 402, 414 and 416) is enable via application 516 as appropriately configured, to communicate an image for processing and return of diagnosis data (e.g. acne data). In such an example, application 516 is configured to perform these activities.

Though not shown, a computing device may be configured as a training environment to train neural network model 514 for example using the network as shown in FIG. 5 along with appropriate training and/or testing data.

The model 418 may be adapted to a light architecture for a computing device that is a mobile device (e.g. a smartphone or tablet) having fewer processing resources than a "larger" device such as a laptop, desktop, workstation, server or other comparable generation computing device.

Though not shown in detail, server devices shown are computing devices similar in basic construction (processors, storage devices, communication devices, input and output devices) to computing device 402 but as server-side device. That is, server devices often are not configured with consumer oriented hardware, having fewer input and output devices, fewer user applications, a server oriented O/S, etc.

Figure 6:
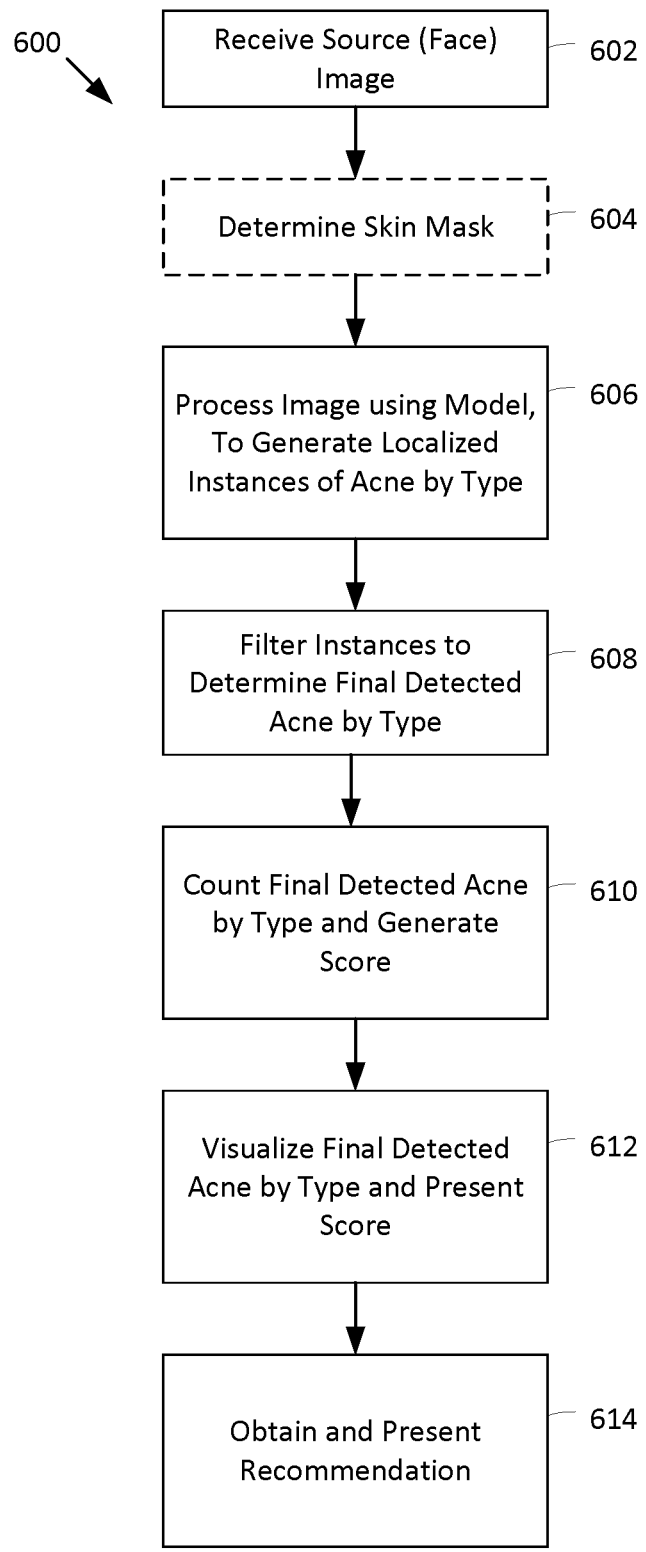
FIG. 6 is a flow chart of operations in accordance with an embodiment.

FIG. 6 is a flow chart of operations 600 in accordance with an embodiment.

At 602, a source (face) image is received. For example the source image is a selfie image captured by a camera of a computing device.

Operations at 604 are optional and shown in broken line style. A face skin mask is determined for use to guide image processing.

At 606 operations process the face image using a model to generate localized instances of acne by type (e.g. one of three classes). In an embodiment, the model is configured to: detect at least one type of acne in images; and focus detection on small objects in images. In an embodiment the model is a first model embodiment. In embodiment the model is a second model embodiment. In an embodiment, processing is guided by a skin mask as produced by operations at 604.

At 608, the instances detected are filtered such as described herein above to select better localizations and instances with higher confidence levels. Thus, final detected acne is determined, by type.

At 610, a count is determined, by type. At 610 a score is generated, for example, representing a severity measure. At 612, the final detected acne is visualized in association with the source image. For example, the image is annotated to show the final detected acne by type. In an embodiment, the image has annotations overlaid thereon. At 612, the score is presented.

At 614 a recommendation is obtained. At 614, the recommendation is presented. In an embodiment, the score is provided to an e-commerce service to generate the recommendation for a product and/or service.

In an embodiment operations 600 may be performed by a single computing device (e.g. device 402), communicating with another device (e.g. 408 and/or 410), as applicable.

In an embodiment, operations are performed by more than one computing device (e.g. 402, 408 and 410). For example, operations at 606 comprise communicating the source image to a computing device 408 providing the model as a service. That computing device 408 may also filter (step 608). That device 408 may also count the acne (step 610). That device 408 may also visualize the acne (step 612) and return the source image overlaid with the visualization and the count and/or a score (e.g. for presenting by device 402). A third computing device 410 may provide the recommendation, for example, in response to a query including the score. In operations 600, steps therein may be divided into more than one step or combined into fewer steps.

Practical implementation may include any or all of the features described herein. These and other aspects, features and various combinations may be expressed as methods, apparatus, systems, means for performing functions, program products, and in other ways, combining the features described herein. A number of embodiments have been described. Nevertheless, it will be understood that various modifications can be made without departing from the spirit and scope of the processes and techniques described herein. In addition, other steps can be provided, or steps can be eliminated, from the described process, and other components can be added to, or removed from, the described systems. Accordingly, other embodiments are within the scope of the following claims.

Throughout the description and claims of this specification, the word "comprise", "contain" and variations of them mean "including but not limited to" and they are not intended to (and do not) exclude other components, integers or steps. Throughout this specification, the singular encompasses the plural unless the context requires otherwise. In particular, where the indefinite article is used, the specification is to be understood as contemplating plurality as well as singularity, unless the context requires otherwise.

Features, integers, characteristics, or groups described in conjunction with a particular aspect, embodiment or example of the invention are to be understood to be applicable to any other aspect, embodiment or example unless incompatible therewith. All of the features disclosed herein (including any accompanying claims, abstract and drawings), and/or all of the steps of any method or process so disclosed, may be combined in any combination, except combinations where at least some of such features and/or steps are mutually exclusive. The invention is not restricted to the details of any foregoing examples or embodiments. The invention extends to any novel one, or any novel combination, of the features disclosed in this specification (including any accompanying claims, abstract and drawings) or to any novel one, or any novel combination, of the steps of any method or process disclosed.

What is claimed is:

1. A method for analyzing skin images comprising: analyzing a source image using a convolutional neural network (CNN) model configured to process the source image pixel-by-pixel and output anchor boxes indicating respective locations of instances of acne;
visualizing the instances of acne on the source image for display by overlaying annotations on the source image showing the location and type of each acne instance based on output from the CNN model;
wherein the CNN model is trained using labelled facial images to:
detect at least one type of acne in images; and
focus detection on acne occurrences in images; and
wherein the CNN model comprises: a YOLO (You Only Look Once)-based model configured to comprise a single detection layer to form a single detection YOLO-based model and further configured to output a plurality of predictions comprising a three dimensional tensor encoding bounding box, objectness, and class predictions, and wherein the plurality of predictions are filtered to eliminate redundant detections of the same acne instance, the single detection layer YOLO-based model having been fine tuned to optimize acne localization accuracy.

2. The method of claim 1, wherein the CNN model is a deep learning neural network model configured for object classification and localization.

3. The method of claim 1, wherein the CNN model is configured to process the source image on a pixel level, operating end-to-end to directly detect acne location.

4. The method of claim 1, wherein the CNN model generates respective anchor boxes providing location information for each of the instances of acne detected.

5. The method of claim 4, wherein an anchor box aspect ratio, for use to define one of the anchor boxes, is calculated using k-means clustering from acne instances identified in a dataset of images.

6. The method of claim 1, wherein visualizing the instances of the acne indicates a respective location for each of the instances on the source image and indicates a respective type of acne for each of the instances on the source image.

7. The method of claim 1, wherein the at least one type of acne includes one or more of retentional acne, inflammatory acne and pigmentary acne.

8. The method of claim 1 comprising determining a count of the instances of acne.

9. The method of claim 1 comprising obtaining a recommendation for one or more of a product and a service specific to treat the instances of the acne.

10. The method of claim 9 comprising communicating with an e-commerce system for making a purchase of the product or service.

11. The method of claim 9, wherein the recommendation is generated in response to factors selected from the group: acne type, count by type, score by type, location of the acne, location of purchaser, delivery location, regulatory requirement, counter indication, gender, co-recommendation, and likelihood of user to follow use guidelines.

12. A computing system for analyzing skin images comprising circuitry configured to provide:
an interface to receive a source image and return an annotated source image which visualizes instances of acne determined by a convolutional neural network (CNN) model configured to process the source image pixel-by-pixel and output anchor boxes indicating respective locations of instances of acne;
wherein the CNN model is configured to:
focus detection on small objects in images; and
detect at least one type of acne in images; and
wherein the CNN model comprises:
a single detection layer YOLO (You Only Look Once)-based model configured to output a plurality of predictions comprising a three dimensional tensor encoding bounding box, objectness, and class predictions, and wherein the plurality of predictions are filtered to eliminate redundant detections of the same acne instance, the single detection layer YOLO-based model being fine tuned to optimize acne localization accuracy.

13. The computing system of claim 12 configured to provide:
a recommendation component configured to recommend a product and/or service to specifically treat at least some of the instances of acne; and,
an e-commerce transaction component to facilitate a purchase of the product and/or service.

14. The computing system of claim 12, wherein the single detection layer YOLO-based model is fine tuned by one or more of:
performing data augmentation on the labelled facial images comprising:
converting the labelled facial images to HSV color space;
adding random color jittering on saturation and value channels of the HSV color space images;
applying random affine transformation on the HSV color space images;
utilizing a multi-step learning rate scheduler during model training; or
employing an evolution algorithm to iteratively adjust parameters of the data augmentation, wherein the evolution algorithm comprises:
training the model through multiple rounds; and
selecting parameters that optimize acne detection.

15. The method of claim 1, wherein the single detection layer YOLO-based model is fine tuned by one or more of:

performing data augmentation on the labelled facial images comprising:
converting the labelled facial images to HSV color space;
adding random color jittering on saturation and value channels of the HSV color space images;
applying random affine transformation on the HSV color space images;
utilizing a multi-step learning rate scheduler during model training; or
employing an evolution algorithm to iteratively adjust parameters of the data augmentation, wherein the evolution algorithm comprises:
training the model through multiple rounds; and
selecting parameters that optimize acne detection.

* * * * *